US010363219B2

(12) United States Patent
Fang et al.

(10) Patent No.: US 10,363,219 B2
(45) Date of Patent: Jul. 30, 2019

(54) METHOD OF PREPARING ALBUMIN NANOPARTICLE CARRIER WRAPPING TAXANE DRUG

(71) Applicant: Zhejiang Academy of Forestry, Hangzhou (CN)

(72) Inventors: Ru Fang, Hangzhou (CN); Shaozong Yang, Hangzhou (CN); Hua Qian, Hangzhou (CN); Yanbin Wang, Hangzhou (CN)

(73) Assignee: Zhejiang Academy of Forestry, Hangzhou (CN)

( * ) Notice: Subject to any disclaimer, the term of this patent is extended or adjusted under 35 U.S.C. 154(b) by 21 days.

(21) Appl. No.: 15/600,732

(22) Filed: May 20, 2017

(65) Prior Publication Data
US 2018/0116963 A1     May 3, 2018

(30) Foreign Application Priority Data
Oct. 28, 2016    (CN) .......................... 2016 1 0966644

(51) Int. Cl.
| A61K 9/00 | (2006.01) |
| A61K 9/16 | (2006.01) |
| A61K 9/19 | (2006.01) |
| A61K 9/51 | (2006.01) |
| A61K 31/337 | (2006.01) |

(52) U.S. Cl.
CPC .......... *A61K 9/1694* (2013.01); *A61K 9/0019* (2013.01); *A61K 9/1658* (2013.01); *A61K 9/19* (2013.01); *A61K 9/5169* (2013.01); *A61K 9/5192* (2013.01); *A61K 31/337* (2013.01)

(58) Field of Classification Search
CPC .. A61K 9/1694; A61K 9/0019; A61K 9/1658; A61K 9/19; A61K 9/5169; A61K 9/5192; A61K 9/337

USPC ......................................................... 424/489
See application file for complete search history.

(56) References Cited

U.S. PATENT DOCUMENTS

2003/0187062 A1* 10/2003 Zenoni ................. A61K 9/0019
                                                                  514/449
2015/0290332 A1* 10/2015 Kim ..................... A61K 31/555
                                                                  530/363

FOREIGN PATENT DOCUMENTS

| CN | 102274190 B | 12/2012 |
| CN | 103169662 A | 6/2013 |
| CN | 104490847 A | 4/2015 |
| CN | 103735514 B | 11/2015 |

* cited by examiner

Primary Examiner — Adam C Milligan
(74) Attorney, Agent, or Firm — Gokalp Bayramoglu

(57) ABSTRACT

The present invention belongs to the field of bio-pharmaceutical material preparation technology, and relates to a preparation method of albumin nanoparticle carrier entrapping taxane-typed drug. This preparation method rapidly forms nanoparticle solution of albumin entrapping taxane-typed drug under room temperature by adding solvent as the medium. Next, by the second time of freeze-drying, stable powder of albumin nanoparticles entrapping taxane-typed drug is obtained. The final freeze-dried powder only includes two components: albumin and taxane-typed drug. The particles are in regular spherical shape, and the diameter of particle is less than 100 nm. The present invention has high drug loading ratio and entrapment efficiency. The experiment of releasing in vitro shows that the present invention has a good slow-release effect. Taxane-typed drug nanoparticles provided by the present invention improves the safety and compliance of this type of reagent.

6 Claims, 3 Drawing Sheets

METHOD OF PREPARING ALBUMIN NANOPARTICLE CARRIER WRAPPING TAXANE DRUG

CROSS REFERENCE

This application claims the priority from Chinese patent application No. 201610966644.5, filed on Oct. 28, 2016, the entire contents of which are incorporated herein by reference.

TECHNICAL FIELD

The present invention relates to a preparation method of albumin nanoparticle carrier, particularly to a preparation method of albumin nanoparticle carrier entrapping taxane-typed drug, belonging to the field of bio-pharmaceutical preparation technology.

BACKGROUND

Paclitaxel is a diterpenoid compound which is separated from leaves and barks of *taxus chinensis* genus of plants. The molecule formula of paclitaxel is $C_{47}H_{51}NO_{24}$. The molecule weight of paclitaxel is 853.94. Paclitaxel can induce tubulin to polymerize, so as to stop the mitosis of cancer cells. Paclitaxel has broad anti-tumor ability, and is mainly used for the treatment of tumors, ovarian cancer, breast cancer, pancreatic cancer, gastric cancer, lung cancer, etc. In 1992, Food and Drug Administration (FDA) approved the use of paclitaxel in treating various cancers. Up to now, more than 40 countries have approved the use of paclitaxel in treating cancers.

Docetaxel is a semisynthetic compound, which is obtained by semi-synthesizing incompetent precursor (10-deacetylbaccatin) that is extracted from European *taxus chinensis*. The molecule formula is $C_{43}H_{53}NO_{14}$. The molecule weight is 807.88. The antitumor mechanism of docetaxel is the same as that of paclitaxel. Docetaxel has good curative effect for treating breast cancer, non-small cell lung cancer, pancreatic cancer, soft tissue sarcoma, gastric cancer, ovarian cancer, prostatic cancer, etc. Compared with paclitaxel, the structure of docetaxel has two modifications. First, on the site C-10 of the ring B of taxol, acetyl is replaced by carboxyl. Second, the C-13 side chain is modified. Differences of chemical structure make docetaxel and paclitaxel different in terms of activity. The cytotoxic effect of docetaxel is 1.3-12 times of that of paclitaxel.

Due to the special structure, the water solubility of taxane-typed drug is very poor, which is less than 1 μg/mL at room temperature. Thus, the key technology in the research of reagent of taxane-typed drug is to improve the solubility of taxane-typed drug in aqueous solution. Currently, liquid injection reagents and freeze-dried powder reagents are mainly and clinically used. Nowadays, liquid injection paclitaxel (Taxol®) on the market uses polyoxyethylated castor oil (Cremphor EL) and absolute ethyl alcohol as solvents, while docetaxel uses polysorbate 80 (Tween 80) and absolute ethyl alcohol as solvents. Although the solubility of the drug is increased by a certain degree, patients have severe allergic reactions, nephrotoxicity, neurotoxicity, cardiotoxicity, hypotension and other adverse reactions after the treatment. Thus, the research on the freeze-dried powder without highly poisonous organic solvent has attracted the attention of researchers.

Nowadays, there are some good methods for preparing freeze-dried powder entrapping taxane-typed drug. For example, Chinese patent application No. CN103169662, published on Jun. 26, 2013, discloses a method for preparing paclitaxel high molecular nanoparticles. This method uses a combination of either one or more of polylactic acid, polyhydroxybutanoic acid, poly (lactic acid-glycolic acid) as raw materials and uses the organic solvent to form emulsified liquid. After rotary evaporation and multiple "high-speed centrifugation-resuscitation" processes and freeze-drying, paclitaxel high-molecular nanoparticle with a particle diameter of 50-800 nm are obtained. In this method, paclitaxel and high-molecular material are just mixed physically, and the functional character of paclitaxel drug does not change. However, the process is complicated and hard to control. Since the paclitaxel and high-molecular material just interact physically, the stability is poor.

For another example, in Chinese patent application No. CN103735514, published on Nov. 25, 2015, a method for preparing nanoparticle modified by polyethylene glycol vitamin E succinate and calreticulin is disclosed. This preparation method uses phospholipids, sophorolipid, calreticulin, polyethylene glycol vitamin E succinate as raw materials, ethanol as mediate, and uses vacuum rotary evaporation to prepare nanoparticles that have an average particle diameter of 100-150 nm and can entrap hydrophobic drug such as paclitaxel, morin, apigenin and so on. In this preparation method, the process is easy to control, and the nanoparticle has a high stability. However, the components of the product obtained are complex such that there is a huge safety risk.

For another example, in Chinese patent application No. CN104490847, published on Apr. 8, 2015, a thermal denaturation method for preparing albumin nanoparticle is disclosed. This method forms stable nanoparticle by adding vanillin or the analogues and through the disulfide bond, amide bond between the albumin molecules and formation of Schiff base and other chemical bonds between albumin molecule and vanillin molecule in the heating condition. No organic solvent is introduced in the preparation process and it is safe and non-toxic. However, this method requires heating to 120° C., which may change the structure and functional feature of taxane-typed drug.

For another example, in Chinese patent application No. CN102274190, published on Dec. 5, 2012, a method for preparing paclitaxel albumin submicron is disclosed. This method uses test butyl alcohol as the emulsifier, effectively embedding paclitaxel into albumin, and uses freeze-drying method to remove tert butyl alcohol. Since carbohydrates or amino acids are used as freeze-drying protective agents in the preparation system, paclitaxel albumin submicron with stable structure is finally obtained. For this method, the process is simple, safe and non-toxic, and the product can be stored for a long time. However, the paclitaxel albumin submicron prepared by this method has a relatively large particle diameter which is 300-500 nm.

So far, paclitaxel albumin binding particles (Abraxane®) developed by Celgene Corporation, a US biopharmaceutical company, is the only nanoparticle freeze-dried powder of paclitaxel approved by FDA. This agent is prepared by using a nanoparticle albumin binding (nab) technique in ABI patent and only comprises albumin and paclitaxel without toxic solvent. This agent is suitable for treating metastatic breast cancer surviving combined chemotherapy or breast cancer relapsing within 6 months after assisted chemotherapy, advanced or metastatic non-small cell carcinoma, and metastatic pancreatic cancer. Compared with Taxol®, the solubility of paclitaxel in Abraxane® is significantly increased such that the occurrence of allergic reaction is significantly reduced. A clinical study of random control phase III for Abraxane® and Taxol® in which 454 patients participated showed that the curative effect on patients of Abraxane® is almost twice as that of Taxol®. In addition, Abraxane® does not contain toxic solvent and has a higher dose than Taxol® such that the anti-tumor effect can be improved.

Albumin is the protein existing in adtevak. Bovine serum albumin (BSA) and human serum albumin (HSA) are commonly used in researches. In addition to safety, non-toxicity, biodegradability, non-immunogenicity and other characteristics, albumin nano-carrier has its own advantages. First, as a natural transport protein, serum albumin has several drug binding sites, including hydrophobic and hydrophilic drugs. Thus, albumin nano-drug carrier has the high drug-loading capacity. Second, albumin nano-drug carrier has a natural transmembrane transport pathway and can achieve the targeted transport of the entrapped drug towards the tumor tissue. Nowadays, common methods for preparing albumin nano-carrier include anti-solvent method, emulsification method, hot gel method, nab technology, self-assembly technology, nano-spray drying, etc. Nab technology is a highly-recognized method for preparing serum albumin nano-drug carrier. In addition to Abraxane® which has been approved by FDA of the US in January 2005, there are a number of other nab technology-based drugs under development, such as ABI-008 (nab-docetaxel), ABI-009 (nab-rapamycin) and so on. However, as an ideal nano-drug carrier, albumin nanoparticle prepared by nab technology still has some disadvantages. The particle diameter of Abraxane® is 130 nm, which, strictly speaking, is not nano-size. The obtained nanoparticie prepared by such method has a poor stability and cannot survive the dilution of the buffer solution, and will aggregate into large particles within 24 hours.

SUMMARY OF THE INVENTION

The purpose of the present invention is to overcome the drawbacks of the prior art and provide a safe, non-toxic, stable, nano-size compatible method of preparing albumin nanoparticle carrier entrapping taxane-typed drug.

The technical solution to solve the above problems used by the present invention is as follows, the preparation method of albumin nanoparticle carrier entrapping taxane-typed drug includes the following steps:

1) Albumin aqueous solution with volume-mass concentration of 20~200 mg/mL is prepared, so as to obtain solution A.
2) Organic compound is used as solvent to prepare solution of taxane-typed drug with volume-mass concentration of 0.5~5 mg/mL, so as to obtain solution B.
3) Pure water and solution A are mixed with a certain ratio, and are stirred at 200~1000 rpm for 3~10 minutes, so as to obtain solution C. The solvent of solution B and solution B are mixed with a certain ratio, and are stirred at 200~1000 rpm for 3~10 min, so as to obtain solution D. Solution C and solution 1) are mixed rapidly, and are stirred at 200~1000 rpm for 3~10 minutes, and stand still at room temperature for 3~20 minutes, so as to obtain solution E. Here, the use of mixing technology is to make albumin, taxane-typed drug and solvent fully mixed and contacted in the aqueous solution system such that albumin interacts with taxane-typed drug molecule to form nanoparticles. Although high-pressure homogenization and ultrasound isometry shear technique have the ability of well mixing and emulsification, it also affects the albumin molecule and destroys its structure. The experimental data show that the natural conformation of protein molecule affects the embedding effect of nanoparticles oar taxane-typed drug.

4) Solution E is pre-frozen for more than 12 hours. The first freeze-drying treatment is conducted. The freeze-drying machine is configured such that the temperature of the cold trap is −30 to −50° C., the vacuum degree is ≤50 Pa, and the freeze-drying time is ≥36 hours, so as to remove organic solvent and water in the system, to obtain amorphous powder. Amorphous powder contains albumin nanoparticles entrapping taxane-typed drug and a small amount of taxane-typed drug that is not entrapped.

5) A certain amount of pure water is added to amorphous powder to redissolve the powder, so as to obtain solution F. Solution F is centrifuged by a freeze high-speed centrifugal machine, under 0~4° C., at 10000~15000 rpm, for 10~30 minutes. Supernatant is taken, so as to obtain solution G. This step is to remove taxane-typed drug that is not entrapped. The rate and time of rotation speed of centrifuge relate to the clearance ratio of taxane-typed drug that is not entrapped.

6) Solution G is pre-frozen for more than 12 hours. The second freeze-drying treatment is conducted. The freeze-drying machine is configured such that the temperature of the cold trap is −30 to −50° C., the vacuum degree is ≤50 Pa, and the freeze-drying time is ≥18 hours. The water in the system is removed, so as to obtain albumin nanoparticles entrapping taxane-typed drug.

Albumin of the present invention includes human serum albumin and recombined human serum albumin. If the protein is replaced by other proteins, such as myohemoglobin and lysozyme, the diameter of the formed particle will be increased. Moreover, after the second time of freeze-drying, the particles are not stable, and will aggregate. Meanwhile, drug loading ratio is reduced significantly.

The taxane-typed drug of the present invention includes paclitaxel and docetaxel and other structure modified derivatives.

Solvents of taxane-typed drug of the present invention can only be one or more selected from the group consisting of n-butyl alcohol, methylbenzene, xylene, dimethyl sulfoxide, acetic anhydride, chlorobenzene, and ethylene glycol phenyl ether. If the solvents are replaced by other common organic solvents such as ethyl alcohol, methyl alcohol, ethyl acetate, and so on, the diameter of particle of albumin will be too large, even causing particles to precipitate.

In the solution E of the present invention, the volume ratio of pure water, solution A, solvent, and solution B is (64~89):1:(0~25):(10~15).

The preparation method of the present invention requires two freeze-drying processes. Water and solvent exist in the first freeze-drying system, while only water exists in the second freeze-drying system. The boiling point of each of n-butyl alcohol, methylbenzene, xylene, dimethyl sulfoxide, acetic anhydride, chlorobenzene and ethylene glycol phenyl ether and other solvent is greater than that of water, i.e., 100° C., the sublimation time is longer than that of water as well. Thus, the first freeze-drying time is ≥36 hours, the second freeze-drying time ≥18 hours.

Sizes of the albumin nanoparticles of the present invention are uniform, the diameter of particle is 15~100 nm. Zeta potential is −25 to −40 mV.

Drug loading ratio of the albumin nanoparticle carrier with respect to taxane-typed drug of the present invention is 6~10%. The entrapment efficiency is 50~80%.

The formation mechanism of albumin nanoparticles encapsulating taxane-typed drug in the present invention is that, through the effect of solvent, directional denaturation of human serum albumin molecule is caused, and the senior conformation is transformed. As hydrophobic micromolecule, taxane-typed drug molecule will get close to hydrophobic group in albumin molecule, and eventually form albumin nanoparticle taking taxane-typed drug as the core. The hydrophilic group of albumin molecule is exposed to the aqueous solution system. In addition, because there are multiple carbonyls in the taxane-typed drug molecule, and there is multiple tyrosine in albumin molecule. Tyrosine has phenolic hydroxyl, which is unstable in the hydrophobic environment. Thus, the phenolic hydroxyl near taxane-typed drug molecule is easy to form a hydrogen bond with carbonyl. Thus, under the combined action of hydrophobic force and hydrogen bond, albumin nanoparticles entrapping taxane-typed drug with a stable structure is formed.

Compared with prior technique, the present invention has the following advantages and effects. The particle diameter of albumin nanoparticle entrapping taxane-typed drug is less than 100 nm, which is nano-size in the strict sense, and the circulation time of the drug in the body is extended and the pesticide effect is enhanced. The surface of the particle carries negative charge, which prevents the aggregation of the particles. Thus, the albumin nanoparticle entrapping taxane-typed drug prepared in the present invention is stable in clinical use and body circulation system. In the preparation process of the present invention, only taxane-typed drug, albumin, solvent, and water are involved, wherein the solvent and water can be fully removed through two freeze-drying processes. Thus, the final product, freeze-dried powder, only includes taxane-typed drug and albumin such that the toxic and side effect brought by organic solvent can be prevented and the safety is enhanced. The formation of nanoparticle of the present invention is through the hydrophobic force, hydrogen bond, Van der Waals' force, and so on, rather than physical function. Thus, the freeze-drying process will not destroy the structure of nanoparticle. Thus, there is no need to add any freeze-drying protective agent in two freeze-drying processes. This ensures that the components of the final product of the present invention only includes taxane-typed drug and albumin. The present invention has the advantages of low operating temperature, and being suitable for drugs that are unstable at high temperature, easy to operate and suitable for industrial production.

DETAILED DESCRIPTION OF INVENTION

Figure 1:
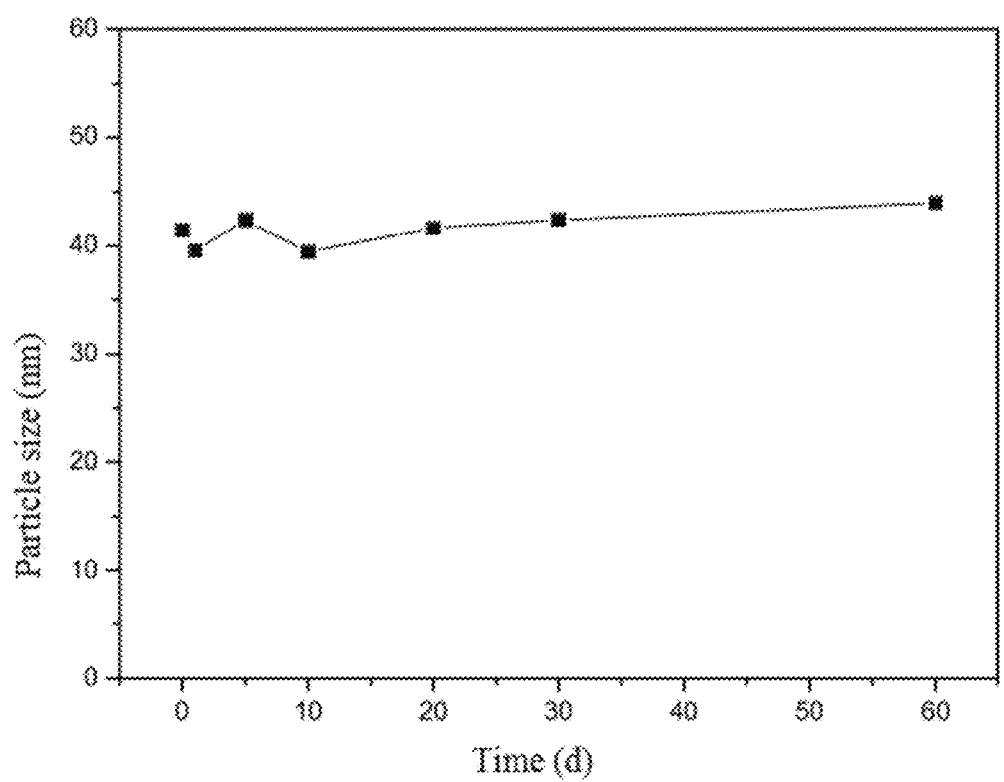
FIG. 1 is the schematic diagram of the curve of stability research of the freeze-dried powder of human serum albumin nanoparticles entrapping paclitaxel of Embodiment 1 of the present invention.
Figure 2:
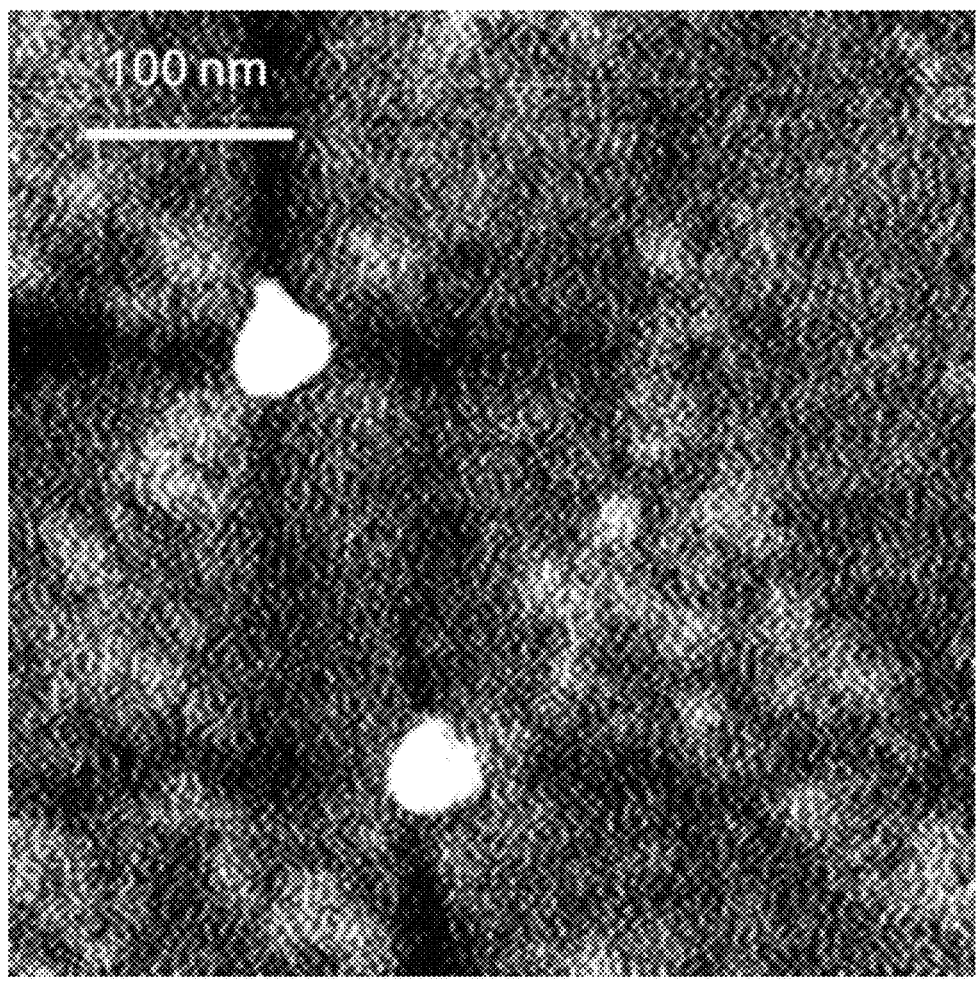
FIG. 2 is the atomic force microscope photo of the freeze-dried powder of human serum albumin nanoparticles entrapping docetaxel of Embodiment 2 of the present invention.
Figure 3:
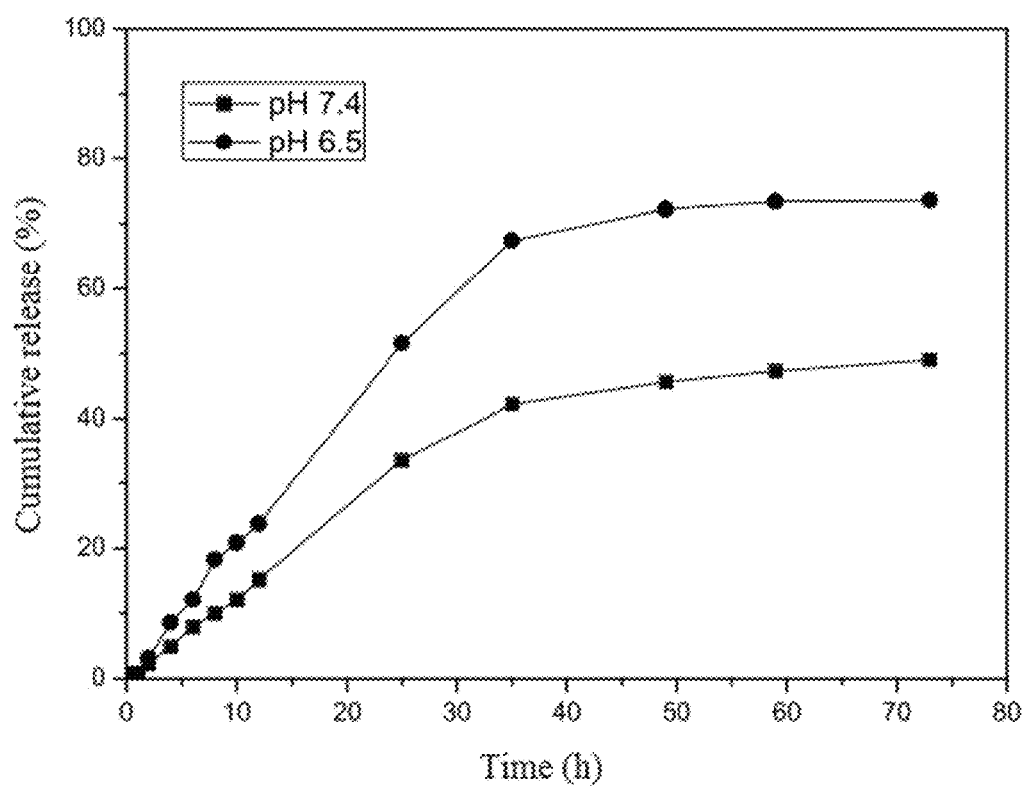
FIG. 3 the schematic diagram of the curve of the freeze-dried powder of human serum albumin nanoparticles entrapping docetaxel of Embodiment 2 of the present invention which is released in vitro under the condition of 37° C.

Hereinafter, the present invention is further described in detail with reference to the drawings and embodiments. The following embodiments are illustrations of the present invention, and the present invention is not limited to the following embodiments.

Embodiment 1

In the present Embodiment, human serum albumin nanoparticles entrapping paclitaxel are prepared. Human serum albumin and paclitaxel are used as raw material to prepare human serum albumin nanoparticles entrapping paclitaxel.

In the present Embodiment, the preparation method of albumin nanoparticle carrier entrapping taxane-typed drug is as below. Human serum albumin aqueous solution with volume-mass concentration of 100 mg/mL is prepared, so as to obtain solution A. Methylbenzene is used as solvent to prepare paclitaxel solution with volume-mass concentration of 2.56 mg/mL, so as to obtain solution B. 87 mL of pure water and 1 mL of solution A are mixed, and are stirred at 800 rpm for 8 minutes, so as to obtain solution C. 2 mL of dimethyl sulfoxide and 10 mL of solution B are mixed, and are stirred at 700 rpm for 6 minutes, so as to obtain solution D. Solution C and solution D are mixed rapidly, and are stirred at 800 rpm for 10 minutes, and stand still at room temperature for 25 minutes, such that 100 mL of solution E containing human serum albumin nanoparticles entrapping paclitaxel is obtained. Solution E is placed in the refrigerator at ~80° C. to freeze for more than 12 hours. The first freeze-drying treatment is conducted for 36 hours, to obtain dried powder. 50 mL of pure water is added to the powder to redissolve the powder, so as to obtain solution F. Solution F is centrifuged by a freeze high-speed centrifugal machine, under 4° C., at 10500 rpm, for 25 minutes. Supernatant is taken, so as to obtain solution G. Solution G is placed in the refrigerator at −80° C. to be frozen for more than 12 hours. The second freeze-drying treatment is conducted for 20 hours, so as to obtain powder of human serum albumin nanoparticles entrapping paclitaxel.

Characteristics of particle: Nano ZS laser particle analyzer is used to detect the diameter of particle and Zeta potential. Results are shown in Table 1. High-performance liquid chromatography is used to determine the absorbance of paclitaxel in the drug-loaded particle. Drug loading ratio and entrapment efficiency of human serum albumin nanoparticle carrier with respect to paclitaxel are calculated according to the formula. Detailed results are shown in Table 1.

Embodiment 2

In the present Embodiment, human serum albumin nanoparticles entrapping docetaxel are prepared. Human serum albumin and docetaxel are used as raw material to prepare human serum albumin nanoparticles entrapping docetaxel.

In the present Embodiment, the preparation method of albumin nanoparticle carrier entrapping taxane-typed drug is as below. Human serum albumin aqueous solution with volume-mass concentration of 100 mg/mL is prepared, so as to obtain solution A. N-butyl alcohol is used as solvent to prepare docetaxel solution with volume-mass concentration of 1.21 mg/mL, so as to obtain solution B. 79 mL of pure water and 1 mL of solution A are mixed, and are stirred at 750 rpm for 8 minutes, so as to obtain solution C. 10 mL of n-butyl alcohol and 10 mL of solution B are mixed, and are stirred at 700 rpm for 6 minutes, so as to obtain solution D. Solution C and solution D are mixed rapidly, and are stirred at 750 rpm for 10 minutes, and kept still at room temperature for 20 minutes, such that 100 mL of solution E containing human serum albumin nanoparticles entrapping docetaxel is obtained. Solution E is placed in the refrigerator at −80° C. to freeze for more than 12 hours. The first freeze-drying treatment is conducted for 36 hours, to obtain dried powder. 50 mL of pure water is added to the powder to redissolve the powder, so as to obtain solution F. Solution F is centrifuged by a freeze high-speed centrifugal machine, under 4° C., at 15000 rpm, for 15 minutes. Supernatant is taken, so as to obtain solution G. Solution G is placed in the refrigerator at −80° C. to freeze for more than 12 hours. The second freeze-drying treatment is conducted for 20 hours, so as to obtain powder of human serum albumin nanoparticles entrapping docetaxel.

Characteristics of particle: Nano ZS laser particle analyzer is used to detect the diameter of particle and Zeta potential. Results are shown in Table 1. High performance liquid chromatography is used to determine the absorbance of paclitaxel in the drug-loaded particle. Drug loading ratio and entrapment efficiency of human serum albumin nanoparticle carrier with respect to paclitaxel are calculated according to the formula. Detailed results are shown in Table 1.

Embodiment 3

In the present Embodiment, recombined human serum albumin nanoparticles entrapping paclitaxel are prepared. Recombined human serum albumin and paclitaxel are used as raw material to prepare recombined human serum albumin nanoparticles entrapping paclitaxel.

In the present Embodiment, the preparation method of albumin nanoparticle carrier entrapping taxane-typed drug is as below. Recombined human serum albumin aqueous solution with volume-mass concentration of 100 mg/mL is prepared, so as to obtain solution A. Ethylene glycol phenyl ether is used as solvent to prepare paclitaxel solution with volume-mass concentration of 1.28 mg/mL, so as to obtain solution B. 34.5 mL of pure water and 1 mL of solution A are mixed, and are stirred at 850 rpm for 7 minutes, so as to obtain solution C. 25 mL of dimethyl sulfoxide and 10 mL of solution B are mixed, and are stirred at 700 rpm for 6 minutes, so as to obtain solution D. Solution C and solution D are mixed rapidly, and are stirred at 850 rpm for 10 minutes, and kept still at room temperature for 30 minutes, such that 100 mL of solution E containing recombined human serum albumin nanoparticles entrapping paclitaxel. Solution E is placed in the refrigerator at −80° C. to freeze for more than 12 hours. The first freeze-drying treatment is conducted for 48 hours, to obtain dried powder. 60 mL of pure water is added to the powder to redissolve the powder, so as to obtain solution F. Solution F is centrifuged by a freeze high-speed centrifugal machine, under 4° C., at 12500 rpm, for 25 minutes. Supernatant is taken, so as to obtain solution G. Solution G is placed in the refrigerator at −80° C. to freeze for more than 12 hours. The second freeze-drying treatment is conducted for 20 hours. The powder of recombined human serum albumin nanoparticles entrapping paclitaxel is obtained.

Characteristics of particle: Nano ZS laser particle analyzer is used to detect the diameter of particle and Zeta potential. Results are shown in Table 1. High-performance liquid chromatography is used to determine the absorbance of paclitaxel in the drug-loaded particle. Drug loading ratio and entrapment efficiency of recombined human serum albumin nanoparticles carrier with respect to paclitaxel are calculated according to the formula. Detailed results are shown in Table 1.

TABLE 1 diameter of albumin nanoparticles entrapping taxane-typed drug, Zeta potential, drug loading ratio, and entrapment efficiency (n = 3)

| | particle diameter (nm) | Zeta potential (mV) | drug loading ratio (%) | entrapment efficiency (%) |
|---|---|---|---|---|
| Embodiment 1 | 42.45 ± 1.39 | 31.53 ± 1.16 | 6.23 ± 0.20 | 54.37 ± 1.17 |
| Embodiment 2 | 48.64 ± 1.71 | 33.30 ± 0.80 | 7.97 ± 0.58 | 81.07 ± 5.15 |
| Embodiment 3 | 73.84 ± 2.51 | 34.03 ± 1.01 | 6.74 ± 0.07 | 57.40 ± 0.62 |

Embodiment 4

In the present Embodiment, the preparation method of albumin nanoparticle carrier entrapping taxane-typed drug includes the following steps:
1) Albumin aqueous solution with volume-mass concentration of 20~200 mg/mL is prepared, so as to obtain solution A.
2) Organic compound is used as solvent to prepare solution of taxane-typed drug with volume-mass concentration of 0.5~5 mg/mL, so as to obtain solution B.
3) Pure water and solution A are mixed, and are stirred at 200~1000 rpm for 3~10 minutes, so as to obtain solution C. The solvent of solution B and solution B are mixed, and are stirred at 200~1000 rpm for 3~10 minutes, so as to obtain solution D. Solution C and solution D are mixed rapidly, and are stirred at 200~1000 rpm for 3~10 minutes, and kept still at room temperature for 3~20 minutes, so as to obtain solution E.
4) Solution E is placed in the refrigerator at −20~80° C. to be pre-frozen for more than 12 hours. Next, the first freeze-drying treatment is conducted. The freeze-drying machine is configured such that the temperature of the cold trap is −30~50° C., the vacuum degree is less than 50 Pa, and the freeze-drying time is more than 36 hours. Dried amorphous powder is obtained.
5) Certain amount of pure water is added to the amorphous powder obtained in step 4) to redissolve the powder, so as to obtain solution F. Solution F is centrifuged by a freeze high-speed centrifugal machine, under 0~4° C., at 10000~15000 rpm, for 10~30 minutes. Supernatant is taken, so as to obtain solution G.
6) Solution G is placed in the refrigerator at −20~80° C. to pre-froze for more than 12 hours. Next, the second freeze-drying treatment is conducted. The freeze-drying machine is configured such that the temperature of the cold trap is −30~50° C., the vacuum degree is less than 50 Pa, and the freeze-drying time is more than 18 hours. The albumin nanoparticles entrapping taxane-typed drug is obtained.

The albumin of the present embodiment can be human serum albumin and/or recombined human serum albumin. Taxane-typed drug includes paclitaxel and docetaxel and one or more than two of derivatives. Solvents of taxane-typed drug can be one or more than two selected from the group consisting of n-butyl alcohol, methylbenzene, xylene, dimethyl sulfoxide, acetic, anhydride, chlorobenzene, and ethylene glycol phenyl ether. In solution E, the volume ratio of pure water, solution A, solvent, and solution B is (64~89):(0~25):(10~15). The sizes of albumin nanoparticles are uniform. The diameter of the particle is 15~100 nm. Zeta potential is −25~−40 mV. Drug loading ratio of albumin nanoparticle carrier with respect to taxane-typed drug is 6~10%. Entrapment efficiency is 50~80%.

By adding solvent as the medium, the present invention rapidly forms nanoparticle solution of albumin entrapping taxane-typed drug under room temperature. Next, by the second time of freeze-drying, stable powder of albumin nanoparticles entrapping taxane-typed drug is obtained. The final freeze-dried powder only includes two components: albumin and taxane-typed drug. The particles are in regular spherical shape, and the diameter of particle is less than 100 nm. The present invention has high drug loading ratio and entrapment efficiency. The experiment of releasing in vitro shows that the present invention has a good slow-release effect. Taxane-typed drug nanoparticles provided by the present invention improves the safety and compliance of this type of reagent. The preparation process of the present invention is simple and practical, easy to repeat, with nice controllability, suitable for industry manufacture, and has good application prospect.

The present invention adds a certain amount of pure water to amorphous powder to redissolve the powder, so as to obtain solution F. Solution F is centrifuged by a freeze high-speed centrifugal machine, under 0~4° C., at 10000~15000 rpm, for 10~30 minutes. Supernatant is taken, so as to obtain solution G. This step is to remove taxane-typed drug that is not entrapped. The rate and time of rotation speed of centrifuge relate to the clearance ratio of taxane-typed drug that is not entrapped. Detailed data are shown in Table 2.

Albumin of the present invention includes human serum albumin and recombined human serum albumin. If the protein is replaced by other proteins, such as myohemoglobin and lysozyme, the diameter of the formed particle will be increased. Moreover, after the second time of freeze-drying, the particles are not stable, and will be polemized. Meanwhile, drug loading ratio is reduced significantly. Detailed data are shown in Table 3.

Solvents of taxane-typed drug of the present invention can only be one or more selected from the group consisting of n-butyl alcohol, methylbenzene, xylene, dimethyl sulfoxide, acetic anhydride, chlorobenzene, and ethylene glycol phenyl ether. If the solvents are replace by common organic solvents such as ethyl alcohol, methyl alcohol, ethyl acetate, and so on, diameter of particle of albumin will be too large, even causing particles to precipitate. Detailed data are shown in Table 4.

TABLE 2 relation between clearance ration of paclitaxel that is not entrapped in Embodiment 1 of the present invention and the centrifuge conditions

| speed (rpm) | time (min) | | |
|---|---|---|---|
| | 5 | 10 | 15 |
| 10,000 | 52% | 61% | 66% |
| 12,000 | 64% | 77% | 81% |
| 15,000 | 75% | 89% | 96% |

TABLE 3 characters of three different kinds of protein nanoparticles entrapping paclitaxel

| | diameter of the 1st freeze-dried particle (nm) | diameter of the 2nd freeze-dried particle (nm) | loading efficiency (%) |
|---|---|---|---|
| human serum albumin | 41.89 ± 1.04 | 42.45 ± 1.39 | 5.53 ± 0.20 |
| myohemoglobin | 75.61 ± 5.37 | 348.27 ± 59.49 | 3.12 ± 0.51 |
| lysozyme | 172.94 ± 15.43 | 637.82 ± 143.81 | 1.47 ± 0.38 |

TABLE 4 diameters of albumin nanoparticles with different organic solvents added

| | concentration (V/V) | | |
|---|---|---|---|
| solvent | 10% | 20% | 30% |
| ethelene glycol monophenyl ether | 42.51 ± 1.24 nm | 57.34 ± 1.86 nm | 73.84 ± 2.51 nm |
| ethyl alcohol | 793.47 ± 105.62 nm | sediment | sediment |
| methyl alcohol | 648.95 ± 141.51 nm | sediment | sediment |
| ethyl acetate | 581.14 ± 92.26 nm | sediment | sediment |

Though embodiments of the present invention are disclosed as above, they are not used to limit the protection scope of the present invention. Alternations, equivalent replacements, improvements, etc. made by a person of ordinary skill in the art without departing the concept and scope of the present invention, all fall into the protection scope of the present invention.

What is claimed is:

1. A method of preparing an albumin nanoparticle carrier, comprising:
   1) preparing an albumin aqueous solution with a volume-mass concentration of 20 to 200 mg/mL to obtain solution A;
   2) preparing a solution of a taxane drug with a volume-mass concentration of 0.5 to 5 mg/mL using an organic compound solvent to obtain solution B, wherein the taxane drug includes one or more items selected from the group consisting of paclitaxel and docetaxel;
   3) mixing pure water and the solution A and stirring at 200-1000 rpm for 3-10 minutes to obtain solution C; mixing additional organic compound solvent and the solution B and stirring at 200 to 1000 rpm for 3 to 10 minutes to obtain solution D; rapidly mixing the solution C and the solution D and stirring at 200 to 1000 rpm for 3 to 10 minutes; standing still at room temperature for 3 to 20 minutes to obtain solution E;
   4) putting the solution E in a refrigerator at −20° C. to −80° C. to pre-freeze for more than 12 hours; next, conducting a first freeze-drying treatment to obtain amorphous powder, wherein a freeze-drying machine is configured such that a temperature of a cold trap is −30° C. to −50° C., a vacuum degree is required to be less than 50 Pa, a freeze-drying time is more than 36 hours;
   5) redissolving the amorphous powder obtained in step 4) by adding pure water to obtain solution F; centrifuging the solution F by a freeze high-speed centrifugal machine at a temperature of 0° C. to 4° C., at 10000 to 15000 rpm, for 10 to 30 minutes; taking supernatant to obtain solution G;

6) putting the solution G in the refrigerator at −20° C. to −80° C. to pre-freeze for more than 12 hours; next, conducting a second freeze-drying treatment to obtain albumin nanoparticles, wherein the freeze-drying machine is configured such that the temperature of the cold trap is −30° C. to −50° C., the vacuum degree is required to be less than 50 Pa, and the freeze-drying time is more than 18 hours.

2. The method of preparing albumin nanoparticle carrier of claim 1, wherein albumin of the albumin aqueous solution is human serum albumin and/or recombined human serum albumin.

3. The method of preparing albumin nanoparticle carrier of claim 1, wherein the organic compound solvent is one or more selected from the group consisting of n-butyl alcohol, methylbenzene, xylene, dimethyl sulfoxide, acetic anhydride, chlorobenzene, and ethylene glycol phenyl ether.

4. The method of preparing albumin nanoparticle carrier of claim 1, wherein in the solution E, a volume ratio of the pure water, the solution A, the solvent, and the solution B is (64-89): 1: (0-25): (10-15).

5. The method of preparing albumin nanoparticle carrier of claim 1, wherein particle sizes of the albumin nanoparticles carrier are uniform, a particle diameter of the albumin nanoparticles carrier is 15 to 100 nm, and zeta potential is −25 to −40 mV.

6. The method of preparing albumin nanoparticle carrier of claim 1, wherein a drug loading ratio of the albumin nanoparticle carrier with respect to the taxane-typed drug is 6% to 10%, and an entrapment efficiency is 50% to 80%.

* * * * *